United States Patent [19]

Gasc et al.

[11] Patent Number: 4,699,907
[45] Date of Patent: Oct. 13, 1987

[54] 4-MORPHOLINYL-1H-INDOLES, PHARMACEUTICAL COMPOSITIONS AND USE

[75] Inventors: Jean-Claude Gasc, Bondy; Lucien Nedelec, La Raincy; Claude Rettien, Montreuil; Dinah W. Nanopoulos, Lyons, all of France

[73] Assignee: Roussel Uclaf, Paris, France

[21] Appl. No.: 941,037

[22] Filed: Dec. 12, 1986

[30] Foreign Application Priority Data

Dec. 13, 1985 [FR] France ............... 85 18482

[51] Int. Cl.$^4$ .................. A61K 31/535; C07D 413/02
[52] U.S. Cl. .................... 514/232; 514/233; 514/234; 514/236; 514/237; 514/238; 544/143
[58] Field of Search ............... 544/143; 514/232, 233, 514/234, 236, 237, 238

[56] References Cited

PUBLICATIONS

Clark, *Chemical Abstracts*, vol. 100, No. 6427z (1984).

*Primary Examiner*—Robert W. Ramsuer
*Attorney, Agent, or Firm*—Bierman & Muserlian

[57] ABSTRACT

Novel racemic mixtures and optical isomers of 4-morpholinyl-1H-indoles of the formula:

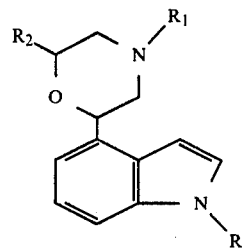

wherein R and $R_1$ are individually selected from the group consisting of hydrogen and alkyl of 1 to 4 carbon atoms and $R_2$ is selected from the group consisting of hydroxymethyl, alkylthiomethyl of 1 to 3 alkyl carbons, cyanomethyl and carboxy optionally esterified with an aliphatic alcohol of 1 to 5 carbon atoms or optionally amidified with an amine of the formula

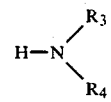

$R_3$ is alkyl of 1 to 4 carbon atoms and $R_4$ is selected from the group consisting of hydrogen and alkyl of 1 to 4 carbon atoms and their non-toxic, pharmaceutically acceptable acid addition salts having the ability to activate neurons and to protect the same against ischemic or anoxic aggressions.

15 Claims, No Drawings

4-MORPHOLINYL-1H-INDOLES, PHARMACEUTICAL COMPOSITIONS AND USE

STATE OF THE ART

French Pat. No. 2,501,208 and No. 2,512,817 and U.S. Pat. No. 4,313,944, No. 4,493,836 and No. 3,901,384 describe various indoles Clark in Journal of Heterocyclic Chemistry (Vol. 20, 1983), pages 1393-1395 describes the preparation of 4-(4-alkyl-2-morpholinyl)-indoles.

OBJECTS OF THE INVENTION

It is an object of the invention to provide the novel 4-morpholinyl-1H-indoles of Formula I and their non-toxic, pharmaceutically acceptable acid addition salts and a process and intermediates for their preparation.

It is another object of the invention to provide novel compositions to combat hypoxia and cerebral ischemia and to a novel method of treating said conditions.

These and other objects and advantages of the invention will become obvious from the following detailed description.

THE INVENTION

The novel compounds of the invention are selected from the group consisting of racemic mixtures and optical isomers of 4-morpholinyl-1H-indoles of the formula:

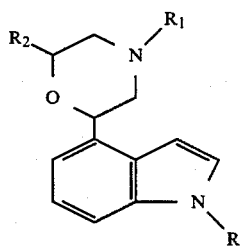

wherein R and $R_1$ are individually selected from the group consisting of hydrogen and alkyl of 1 to 4 carbon atoms and $R_2$ is selected from the group consisting of hydroxymethyl, alkylthiomethyl of 1 to 3 alkyl carbons, cyanomethyl and carboxy optionally esterified with an aliphatic alcohol of 1 to 5 carbon atoms or optionally amidified with an amine of the formula

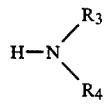

$R_3$ is alkyl of 1 to 4 carbon atoms and $R_4$ is selected from the group consisting of hydrogen and alkyl of 1 to 4 carbon atoms and their non-toxic, pharmaceutically acceptable acid addition salts.

Examples of alkyl in the compounds of Formula I are methyl, ethyl, propyl and isopropyl and examples of the aliphatic alcohols of 1 to 5 carbon atoms are methanol, ethanol, propanol and isopropanol. Examples of alkyl thiomethyls are n-propylthiomethyl, ethylthiomethyl and preferably methylthiomethyl.

Examples of suitable acids for the preparation of the non-toxic, pharmaceutically acceptable acid addition salts are mineral acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, arylsulfonic acids such as benzene sulfonic acid and p-toluene sulfonic acid and arylcarboxylic acids such as benzoic acid.

Among the preferred compounds of Formula I are those wherein R is hydrogen and those wherein $R_2$ is hydroxymethyl, alkylthiomethyl, cyanomethyl, carboxy and

wherein $R_4$ and $R_5$ are linear alkyl of 1 to 4 carbon atoms and their non-toxic, pharmaceutically acceptable acid addition salts. Especially preferred are compounds of Formula I wherein $R_2$ is alkylthiomethyl and a specific compound is 4-[(2R-cis)-4-methyl-6-methylthiomethyl-2-morpholinyl]-1H-indole and its acid addition salts.

The novel process of the invention for the preparation of the compounds of Formula I comprises submitting a compound of the formula

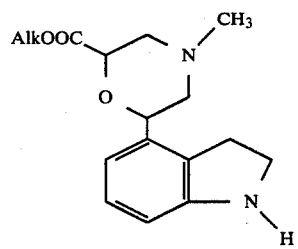

wherein Alk is an alkyl of 1 to 4 carbon atoms to dehydrogenation to obtain a compound of the formula

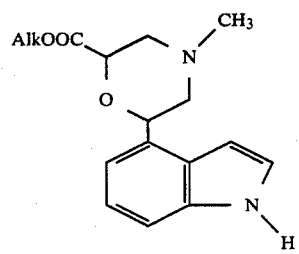

which may be isolated and optionally salified or dimethylated to obtain a compound of the formula

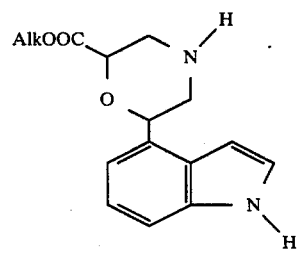

which may be isolated and optionally salified or reacted with an alkylation agent to obtain a compound of the formula

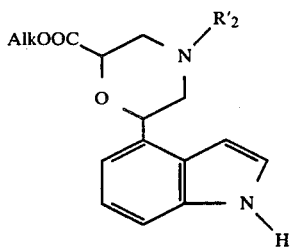

wherein R'₂ is R₂ other than hydrogen which may be isolated and optionally salified or reacted with an alkali metal amide and then an alkyl halide R'-Hal wherein R' is alkyl of 1 to 4 carbon atoms and Hal is chlorine, bromine or iodine to obtain a compound of the formula

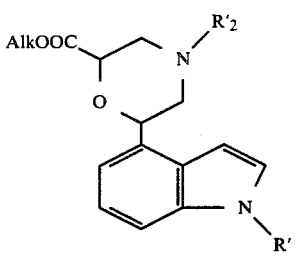

which may be isolated and optionally salified or is subjected to saponification to obtain a compound of the formula

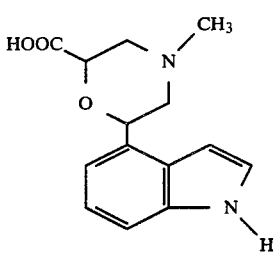

which may be isolated and optionally salified or reacted with an amine of the formula

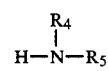

wherein R₄ and R₅ have the above definitions to obtain a compound of the formula

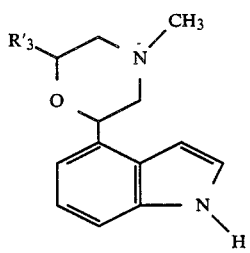

wherein R'₃ is

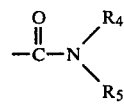

which may be isolated and optionally salified or the compound of Formula $I_A$ may be reduced to form a compound of the formula

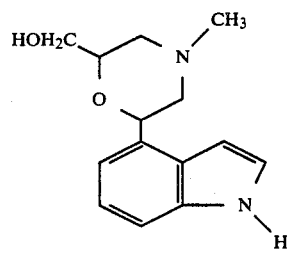

which may be isolated and optionally salified or reacted with methane sulfonyl chloride on p-toluene sulfonyl chloride to obtain a compound of the formula

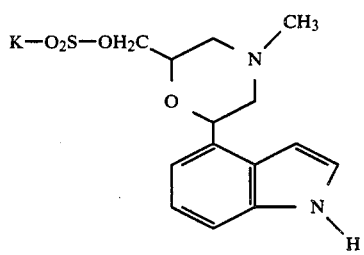

wherein K is methyl or p-tolyl and reacting the latter with an alkali metal cyanide or alkylmercaptan to obtain a compound of the formula

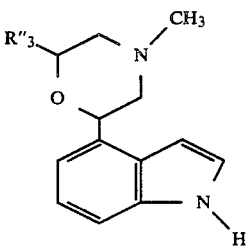

wherein R"₃ is cyanomethyl or alkylthiomethyl which may be isolated and optionally salified and optionally submitting the compounds of Formulae $I_E$, $I_F$, $I_G$ and $I_H$ to one or more of the reactions the compounds of Formula $I_A$ were submitted to and optionally salifying the corresponding compounds of Formula I.

In a preferred mode of the process of the invention, the compound of Formula II is dehydrogenated with manganese dioxide or with oxygen in the presence of a metal such as palladium or selenium. The demethylation of the product of Formula $I_A$ is effected preferably by reaction with cyanogen bromide followed by a reduction such as by the action of zinc in acetic acid. The alkylation of the compound of Formula $I_B$ is effected preferably with an alkyl halide, particularly an alkyl iodide, in the presence of a condensation agent such as an alkali metal carbonate.

The halide of Formula IV can be a chloride or a bromide, but preferably an iodide and is reacted after action, particularly in ammonia, of an alkali metal amide, preferably sodium amide, on the product of Formula $I_C$. The saponification of the compound of Formula $I_A$ is effected preferably by the action of a strong base such as 2N sodium hydroxide or preferably an alkali metal alcoholate such as sodium methylate; a hydrolysis in an acid medium can also be carried out, for example by the action of a mineral acid such as dilute hydrochloric acid in a solvent such as an alkanol of 1 to 5 carbon atoms, in particular ethanol.

The reaction of the compound of Formula $I_E$ with the amine of Formula V to form the compound of Formula $I_F$ is effected preferably after activation of the carboxylic acid function by formation of a mixed anhydride, for example, by the action of trifluoroacetic anhydride or an alkyl haloformate such as isobutyl chloroformate. The reduction of the compound of Formula $I_A$ is effected preferably by the action of sodium borohydride at reflux of a solvent such as dioxane or a dioxane-methanol or dioxane-ethanol mixture; other reducing agents such as sodium cyano-borohydride can also be used.

The reaction of the compound of Formula $I_G$ with methane sulfonyl chloride or p-toluene sulfonyl chloride is effected preferably in pyridine at ambient temperature. The reaction of the compound of Formula VI with alkylmercaptan is effected preferably at ambient temperature in a solvent such as dimethylacetamide in the presence of sodium hydride and the alkylmercaptan is preferably methylmercaptan. The alkali metal cyanide which is reacted with the compound of Formula VI is preferably sodium or potassium cyanide and the operation is advantageously effected in a solvent such as dimethylformamide.

The compounds of Formula I, with the exception of compounds wherein $R_2$ is free carboxy, show a basic character and the addition salts of compounds of Formula I can advantageously be prepared by reaction with a mineral or organic acid, preferably stoichiometric proportions, with the said compounds of Formula I. The salts can be prepared without isolating the corresponding bases.

The starting compounds of Formula II can be prepared, for example, by reacting a compound of the formula

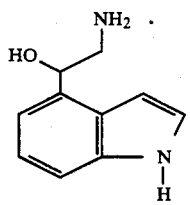

with a methyl haloformate wherein the halogen is bromine or preferably, chlorine, to obtain a compound of the formula

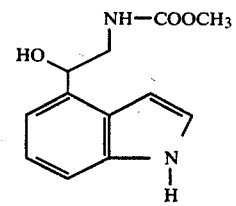

which is reduced, preferably with boranetrimethylamine complex to obtain a compound of the formula

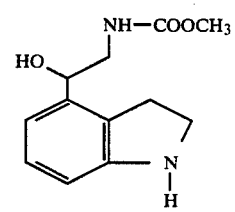

which is reacted with a halide, preferably benzyl chloride, to obtain a compound of the formula

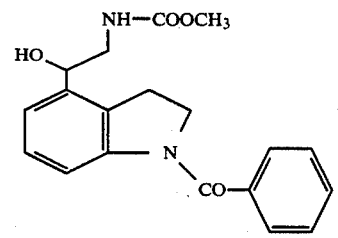

which is reduced, preferably with aluminium-lithium hydride, to obtain a compound of the formula

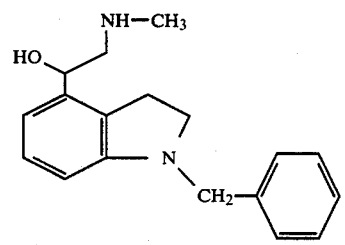

which is reacted with an alkyl glycidate of the formula

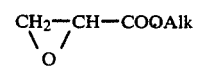

wherein Alk has the above definition to obtain a compound of the formula

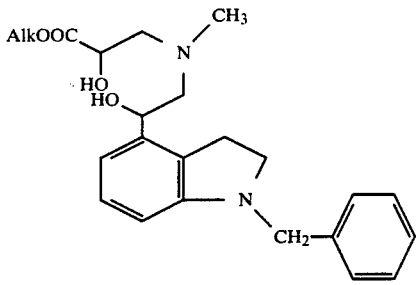

(XIII)

in which Alk has the significance already indicated, which is cyclized, for example by the action of N-chloro-diisopropylamine in the presence of hexamethylphosphoramine or, preferably, of trisdimethylaminophosphine, to obtain a product of the formula

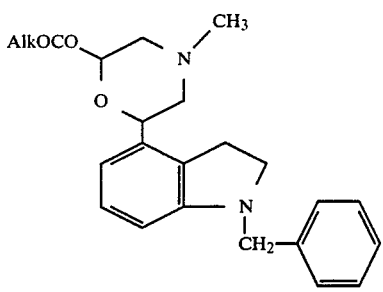

(XIV)

in which Alk has the significance already indicated which is debenzylated, for example, by catalytic hydrogenation, to obtain the product sought of Formula II.

The novel antihypoxia and anticerebral ischemia compositions of the invention are comprised of an antihypoxially and anticerbral ischemically effective amount of at least one compound of Formula I and their non-toxic, pharmaceutically acceptable acid addition salts and an inert pharmaceutical carrier or excipient. The compositions may be in the form of tablets, dragees, capsules, granules, suppositories or injectable solutions or suspensions.

Examples of suitable excipients are talc, arabic gum, lactose, starch, magnesium stearate, cocoa butter, aqueous and non-aqueous vehicles, fatty substances of animal and vegetable origin, paraffin derivatives, glycols, various wetting, dispersing or emulsifying agents and preservatives.

The compositions of the invention protect neurons against ischemic or anoxic aggressions and ensure their activation and they improve the cognitive processes. They are useful in the treatment of essential arterial hypertension, of hypertension of fifty-year olds, of menopause, of the diabetic, of obese and plethoric, as well as in the treatment of arterial hypertension of old people or people affected with arteriosclerosis and in the treatment of hypertension originating in the kidneys. They can also be used in the treatment of cerebral degeneration and senescence or manifestations connected with cerebral hypoxia.

The novel method of the invention of treating cerebral hypoxia and ischemia in warm-blooded animals, including humans, comprises administering to warm-blooded animals an amount of at least one compound of Formula I and their non-toxic, pharmaceutically acceptable acid addition salts sufficient to combat cerebral hypoxia and ischemia. The compounds may be administered orally, rectally or parenterally and the usual daily dose is 0.07 to 2.8 mg/kg depending on the condition treated, the specific compound and the method of administration. For example, the compound of example 3 may be administered at 0.07 to 0.7 mg/kg for treating cerebral senescene.

The novel intermediates of the invention are the compounds of the formula

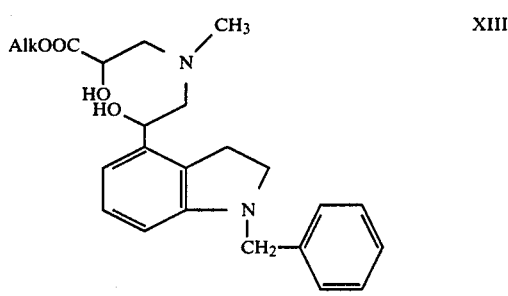

XIII wherein Alk is alkyl of 1 to 4 carbon atoms.

In the following examples there are described several preferred embodiments to illustrate the invention. However, it should be understood that the invention is not intended to be limited to the specific embodiments.

EXAMPLE 1

Ethyl (2RS, 6RS)6-(1H-indole-4-yl)-4-methyl-2-morpholine carboxylate

Step A: Methyl N-[2-(1H-indol-4-yl)-2-hydroxyethyl]carbamate

A solution of 94 ml of methyl chloroformate in 285 ml of ethyl acetate was added dropwise with stirring to a suspension of 285 g of α-(aminoethyl)-1H-indole-4-methanol fumarate and 270 g of sodium bicarbonate in 2,850 ml of water and 2,850 ml of ethyl acetate. After stirring for 1 hour, the decanted aqueous phase was extracted with ethyl acetate. The combined organic phases were washed with a saturated aqueous solution of sodium chloride, dried and evaporated to dryness. The residue was dissolved in methylene chloride, evaporated to dryness and the residue was dissolved in 500 ml of hot methanol. The solution was cooled and isopropyl ether was added. The insoluble matter was filtered off and the filtrate was evaporated to obtain 202 g of methyl N-[2-(1H-indole-4-yl)-2-hydroxyethyl]carbamate.

Step B: Methyl N-[2-(2,3-dihydro-1H-indol-4-yl)-2-hydroxyethyl]carbamate 35.5 g of borane-trimethylamine complex and then, slowly and while cooling to 10° C., 40.55 ml of 12N hydrochloric acid aqueous solution were added to a solution of 22.8 g of the product of Step A in 570 ml of dioxane and the mixture was stirred for 16 hours at ambient temperature. It was poured into 1,500 ml of water, washed with ethyl acetate, made alkaline with 48 ml of concentrated ammonia and was extracted with ethyl acetate. The organic phases were dried, filtered and evaporated to dryness to obtain 22.6 g of methyl N-[2-(2,3-dihydro-1H-indol-4-yl)-2-hydroxyethyl]carbamate which was crystallized from methanol to obtain 13.125 g of the product melting at ≃174° C.

Step C: Methyl N-[2-(1-benzoyl-2,3-dihydro-1-H-indol-4-yl)-2-hydroxyethyl]carbamate 66.6 ml of benzoyl chloride were dropwise with stirring under an inert atmosphere over 10 minutes to an emulsion of 90.3 g of product of Step B in 2,000 ml of chloroform and 573 ml of N sodium hydroxide. After 2 hours 30 minutes of stirring, the mixture was diluted with 1 liter of water. The decanted aqueous phase was extracted with chloroform and the organic phase was washed with water, dried, evaporated to dryness under reduced pressure and crystallized from ethyl acetate to obtain 113.5 g ofm ethylN-[2-(1-benzoyl-2,3-dihydro-1H-indol-4-yl)-2-hydroxyethyl]carbamate melting at 143° C.

Step D: 2,3-dihydro-α-[(methylamino)-methyl]-1-benzyl-1H-indol-4-methanol

A solution of 113 g of the compound of Step C in 1,130 ml of dioxane was added slowly with stirring under an inert atmosphere to a suspension of 110 g of aluminium-lithium hydride and 55 g of aluminium chloride in 1,700 ml of dioxane. After 1 hour of stirring betweeen 80° C. and 50° C. and cooling to 10° C., the excess hydride was destroyed with an ammonium chloride-dioxane-water mixture. The resulting mixture was diluted with water, filtered, and the filtrate was concentrated by eliminating about 1,000 ml of solvent. After adding water and extracting with methylene chloride, the extracts were washed with water saturated with sodium chloride, dried and evaporated to dryness to obtain 95 g of crude product. The crude product was refluxed with stirring in 1 liter of ethyl acetate and 8.5 g of insoluble matter corresponding to the hydrochloride of the expected product were filtered off and melted at ≃179° C. The filtrate was concentrated hot to 400 ml, left to crystallize to obtain 55.19 g of 2,3-dihydro-α-[(methylamino)-methyl]-1-benzyl-1H-indol-4-methanol melting at ≃112° C.

Step E: ethyl 3-[[2-[2,3-dihydro-1-benzyl-1H-indol-4-yl]-2-hydroxy-ethyl]methylamino]-2-hydroxy propanoate 51.1 g of the product of Step D were refluxed for 4 hours with stirring under an inert atmosphere with 511 ml of 100% ethanol and 39 ml of ethyl glycidate and after evaporating at 40° C. under reduced pressure (20 mm, then 0.5 mm Hg), 81.2 g of impure ethyl 3-[[2-[2,3-dihydro-1-benzyl-1H-indol-4-yl]-2-hydroxy-ethyl]methylamino]-2-hydroxy propanoate which was used as is in the following stages.

Step F: ethyl (2RS, 6RS) 6-[2,3-dihydro-1-(benzyl)-1H-indol-4-yl]-4-methyl-2-morpholine carboxylate 8.03 g of the compound of Step E were dissolved in 70 ml of methylene chloride and then cooled to −40° C. 9.13 ml of N-chloro-diisopropylamine were added under an inert atmosphere and then slowly, 11 ml of trisdimethylaminophosphine were added. After stirring for 15 minutes at −40° C., the temperature was allowed to rise. The mixture was diluted with 70 ml of methylene chloride, washed with water, then washed with water saturated with sodium chloride, dried and evaporated to dryness, chromatographed over silica (eluant: benzene-ethyl acetate 7-3 with 0.5% triethylamine) to obtain 4.706 g of ethyl (2RS, 6RS) 6-[2,3-dihydro-1-(benzyl)-1H-4-yl]-4-methyl-2-morpholine carboxylate with an Rf-0.12.

Step G: ethyl (2RS, 6RS) 6-(2,3-dihydro-1H-indol-4-yl)-4-methyl-2-morpholine carboxylate 4.7 g of the compound of Step F were dissolved in 235 ml of acetic acid and 1.18 g of palladium at 10% on charcoal were added. Hydrogen was passed for 1 hour, followed by filtering, evaporating to dryness, taking up in 200 ml of water, and alkalizing to pH 9 with concentrated ammonia. Extraction was with methylene chloride and the extracts were dried and evaporated to dryness to obtain 2.683 g of ethyl (2RS, 6RS) 6-(2,3-dihydro-1H-indole-4-yl)-4-methyl-2-morpholine carboxylate which after crystallization from isopropyl ether melted at ≃92° C.

Step H: ethyl (2RS, 6RS) 6-(1H-indol-4-yl)-4-methyl-2-morpholine carboxylate 3.45 g of ethyl (2RS, 6RS) 6-(2,3-dihydro-1H-indol-4-yl)-4-methyl-2-morpholine carboxylate were dissolved in 345 ml of methylene chloride and 13.8 g of active manganese dioxide were added. The mixture was stirred for 30 minutes, filtered and washed with methylene chloride. The organic phase was evaporated to dryness under reduced pressure to obtain 3.185 g of ethyl (2RS, 6RS) 6-(1H-indole-4-yl)-4-methyl-2-morpholine carboxylate.

EXAMPLE 2

N,N-diethyl 6-(1H-indol-4-yl)-4-methyl-2-morpholine carboxamide and its mesylate A mixture of 4.5 g of ethyl (2RS, 6RS) 6-(1H-indol-4-yl)-4-methyl-2-morpholine carboxylate in 45 ml of methanol was stirred for 65 hours under inert atmosphere with 31.21 ml of a solution of 0.5M of sodium methylate in methanol and was then evaporated to dryness to obtain 4.33 g of the sodium salt of the acid which was used as is for the next stage. The 4.33 g of product were added with stirring under inert atmosphere to 75 ml of dioxane and 90 ml of dimethylformamide and 5.48 ml of tributylamine were added at 10° C. Then, 3 ml of isobutyl chloroformate were added dropwise and after stirring for 90 minutes, 7.93 ml of diethylamine were added dropwise. The mixture was stirred for 4 hours and 30 minutes and evaporated to dryness under reduced pressure. The dry residue was dissolved in water and the solution was extracted with chloroform. The extracts were washed with water, dried and evaporated to dryness and the residue was chromatographed over silica (eluant: methylene chloride/isopropanol 9/1), treated with activated charcoal and chromatographed over silica (eluant: methylene chloride-isopropanol 85-15) to obtain 0.888 g of the desired carboxamide.

The said product was dissolved in isopropanol and 2.82 ml of a solution of 1M/l of methane sulfonic acid in isopropanol were added. The mixture was slightly concentrated and 8 ml of isopropyl ether were added to obtain 1.107 mg of the expected mesylate melting at ≃110°–115° C.

Analysis: $C_{19}H_{29}N_3O_5S$; molecular weight=411.52.

| | C % | H % | N % | S % |
|---|---|---|---|---|
| Calculated: | 55.46 | 7.10 | 10.21 | 7.79 |
| Found: | 55.5 | 7.6 | 9.4 | 6.7 |

EXAMPLE 3

(2RS, 6RS) 6-(1H-indol-4-yl)-4-methyl-2-morpholine methanol and its neutral fumarate 3.185 g of sodium borohydride were added to a solution of 3.185 g of the carbonamide product of Example 2 in 40 ml of methanol and 20 ml of dioxane and the mixture was reluxed with stirring for 1 hour and was then cooled and diluted with 400 ml of water. After extraction with methylene chloride, the extracts were dried and evaporated to dryness under reduced pressure and chromatographed over silica (eluant: methylene chloride-methanol 88-12) to obtain 2.105 g of the desired methanol product.

The said product was dissolved in methanol and a solution of fumaric acid in methanol was added to obtain 2.238 g of the neutral fumarate melting at ≃263° C. with decomposition.

EXAMPLE 4

4-[(2R-cis) 4-methyl-6-[(methylthio)methyl]-2-morpholinyl]-1H-indole (dl) and its neutral fumarate Step A: (2RS, 6RS) 6-(1H-indole-4-yl)-4-methyl-2-morpholine p-toluene sulfonate methanol A solution of 8.58 g of tosyl chloride in 43 ml of pyridine was added dropwise at 10° C. with stirring under an inert atmosphere to a solution of 5.542 g of the base of Example 3 in 55 ml of pyridine and the mixture was stirred for 3 hours at 10° C. and left to rest at 5° C. for about 65 hours. It was then poured into 500 ml of iced water, and after extraction with methylene chloride, the extracts were washed with an aqueous solution of sodium bicarbonate, dried, evaporated to dryness under reduced pressure and chromatographed over silica (eluant: methylene chloride-acetone 1-1) to obtain 7.7 g of (2RS, 6RS) 6-(1H-indole-4-yl)-4-methyl-2-morpholine p-toluene sulfonate methanol.

Step B: 4-[(2R-cis) 4-methyl-6-[(methylthio)methyl]-2-morpholinyl]-1H-indole (dl) and its neutral fumarate 25 ml of dimethylacetamide were added to 9 ml of methyl mercaptan at 0° C. with stirring under an inert atmosphere and then 1.8 g of sodium hydride at 55% in oil were slowly added. After stirring for 90 minutes, 2.5 g of the product of Step A in 15 ml of dimethylacetamide were added and the mixture was stirred for another 2 hours at ambient temperature. It was then poured into 400 ml of iced water and extracted with ethyl acetate. The extracts were washed with water and with a saturated aqueous solution of sodium chloride, dried and evaporated to dryness, chromatographed over silica (eluant: methylene chloride-isopropanol 95-5) to obtain 1.165 g of the expected indole product which after crystallization from isopropanol melted at 156° C.

By addition of a solution of fumaric acid in methanol to a solution of 1.105 g of the said product dissolved in isopropanol, 1.124 g of the expected fumarate melting at 130° C. and then 220° C. were obtained.

EXAMPLE 5

(2SR, 6RS) 6-(1H-indol-4-yl)-4-methyl-2-morpholine acetonitrile and its neutral fumarate 5 g of sodium cyanide were added to a solution of 2 g of the product of Step A of Example 4 in 20 ml of dimethyl sulfoxide and 5 ml of water and the mixture was heated to 60° C. for 18 hours. The reaction mixture was poured into water and extracted with methylene chloride. The extracts were washed with water, dried and evaporated to dryness. The residue was chromatographed over silica (elutant: methylene chloride/methanol 95/5) to obtain 1.24 g of (2RS, 6RS) 6-(1H-indole-4-yl)-4-methyl-2-morpholine acetonitrile.

A solution of 332 mg of fumaric acid in 10 ml of methanol was added to 5 ml of a methanol solution of 1.32 g of the said product and the mixture was evaporated to dryness. The product was crystallized from ethanol at 95° C. to obtain 1.40 g of the fumarate melting at ≃206° C.

UV spectrum in 0.1N hydrochloric ethanol.

| Max. | 213-220 nm | $E_1^1 = 1,355$ | $\epsilon = 42,500$ |
|---|---|---|---|
| Infl. | 249 nm | $E_1^1 = 68$ | |
| Infl. | 273 nm | $E_1^1 = 244$ | |
| Max. | 280 nm | $E_1^1 = 267$ | $\epsilon = 8,350$ |
| Max. | 288 nm | $E_1^1 = 245$ | $\epsilon = 7,650$ |

EXAMPLE 6

Tablets were prepared containing 10 mg of the neutral fumarate of 4-[(2R, cis)-4-methyl-6-(methylthiomethyl)-2-morpholinyl]-1H-indole (dl) and sufficient excipient of starch, lactose, magnesium stearate and talc for a final weight of 100 mg.

PHARMACOLOGICAL DATA

A: Test of labyrinth in T after partial lesion of the septo hippocampic route

By means of an electrolytic partial lesion of neurons of the septo-hippocampic route, a disfunction of the cognitive faculty was provoked in male rats having acquired an apprenticeship in a labyrinth in the form of a T and then the speed of recovery of the disturbed memory faculties was measured. The animals got accustomed to their new environment on days −9 to −6 and rested on days −5 and −4. Their apprenticeship was carried out on days −3 to 0. At this time, the response of the rats was positive at 75–80%. On day 0, the lesion was carried out and the animals rested on days +1 to +3. The animals were tested on day +4 and at this time, only 50% of the responses were positive. From day +5 to +8, the rats were tested after being treated orally with the products under test 1 hour earlier. On day +11, the rats were tested without treatment. The percentage of positive responses of the treated animals were compared in relation to the untreated animals. The product of Example 4 significantly improved the recovery of the memory functions at a dose of 20 mg/kg and therefore, it improved the cognitive processes.

B: Test for enolase

Injured cerebral cells release enolase γγ which is a specific indicator of neuron lesions. The lesions were brought about in mice by sub-cutaneous injection of 35 mg/kg of kainic acid. The test product was administered intraperitoneally at a dose of 1 mg/kg one hour before the injection of the neurotoxin, kainic acid. A protector of the cerebral cells in the injured area decreases the serous concentration of enolase. The product of Example 4 at a dose of 1 mg/kg decreased the serous concentration of enolase γγ by 34% and is therefore, a protector of neuron cells.

C: Test for neuron activation

Neuron activation causes an increase in the corresponding metabolism which is shown by an increase in the consumption of glucose, a proof of energy consumption. This increase was evaluated by measuring the accumulation in the neuron cells of 2deoxyglucose-6-phosphate stemming from the conversion by hexokinase of 2-deoxyglucose $^{14}$C, an analogue of glucose, administered as a tracer dose, which used the same route of entry into the cell as glucose. It was observed that the product of Example 4 caused an increase in the accumulation of 2-deoxyglucose 6-P in the hippocampus of the rat and it therefore, activated selectively the metabolism of certain mesolimbic structures.

D: Acute toxicity study

The lethal doses $LD_O$ of the different compounds tested were evaluated after oral administration to mice. The maximum dose which does not cause mortality in 8 days was called the $LD_O$ and the results obtained are in the following Table.

| Product of example | $LD_O$ in mg/kg |
| --- | --- |
| 2 | ≧200 |
| 3 | ≧400 |
| 4 | 200 |
| 5 | ≧200 |

Various modifications of the products and method of the invention may be made without departing from the spirit or scope thereof and it is to be understood that the invention is intended to be limited only as defined in appended claims.

What we claim is:

1. A compound selected from the group consisting of racemic mixtures and optical isomers of 4-morpholinyl-1H-indoles of the formula:

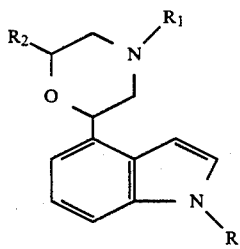

wherein R and $R_1$ are individually selected from the group consisting of hydrogen and alkyl of 1 to 4 carbon atoms and $R_2$ is selected from the group consisting of hydroxymethyl, alkylthiomethyl of 1 to 3 alkyl carbons, cyanomethyl and carboxy optionally esterified with an aliphatic alcohol of 1 to 5 carbon atoms or optionally amidified with an amine of the formula

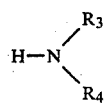

$R_3$ is alkyl of 1 to 4 carbon atoms and $R_4$ is selected from the group consisting of hydrogen and alkyl of 1 to 4 carbon atoms and their non-toxic, pharmaceutically acceptable acid addition salts.

2. A compound of claim 1 wherein R is hydrogen.

3. A compound of claim 2 wherein $R_2$ is selected from the group consisting of hydroxymethyl, alkylthiomethyl of 1 to 4 alkyl carbon atoms, cyanomethyl, —COOH and

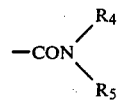

and $R_4$ and $R_5$ are linear alkyl of 1 to 4 carbon atoms.

4. A compound of claim 3 wherein $R_2$ is alkylthiomethyl.

5. A compound of claim 1 selected from the group consisting of 4-[(2RS, cis)-4-methyl-6-(methylthiomethyl)-2-morpholinyl]-1H-indole and its non-toxic, pharmaceutically acceptable acid addition salts.

6. An antihypoxia and antiischemia composition comprising an antihypoxially and antiischemically effective amount of at least one compound of claim 1 and an inert pharmaceutical carrier.

7. A composition of claim 6 wherein R is hydrogen.

8. A composition of claim 7 wherein $R_2$ is selected from the group consisting of hydroxymethyl, alkylthiomethyl of 1 to 4 alkyl carbon atoms, cyanomethyl, —COOH and

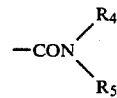

and $R_4$ and $R_5$ are linear alkyl of 1 to 4 carbon atoms.

9. A composition of claim 8 wherein $R_2$ is alkylthiomethyl.

10. A composition of claim 6 wherein the active compound is selected from the group consisting of 4-[(2R, cis)-4-methyl-6-(methylthiomethyl)-2-morpholinyl]-1H-indole and its non-toxic, pharmaceutically acceptable acid addition salts.

11. A method of relieving cerebral hypoxia and ischemia in warm-blooded animals comprising administering to warm-blooded animals an amount of at least one compound of claim 1 sufficient to treat cerebral hypoxia and ischemia.

12. A method of claim 11 wherein R is hydrogen.

13. A method of claim 12 wherein $R_2$ is selected from the group consisting of hydroxymethyl, alkylthiomethyl of 1 to 4 alkyl carbon atoms, cyanomethyl, —COOH and

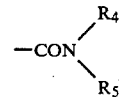

and $R_4$ and $R_5$ are linear alkyl of 1 to 4 carbon atoms.

14. A method of claim 13 wherein $R_2$ is alkylthiomethyl.

15. A method of claim 11 wherein the active compound is selected from the group consisting of 4-[(2R, cis)-4-methyl-6-(methylthiomethyl)-2-morpholinyl]-1H-indole and its non-toxic, pharmaceutically acceptable acid addition salts.

* * * * *